United States Patent [19]

Dennis et al.

[11] Patent Number: 4,482,749
[45] Date of Patent: Nov. 13, 1984

[54] HYDROFORMYLATION PROCESS

[75] Inventors: Alan J. Dennis, Middlesbrough; George E. Harrison, Billericay; James P. Wyber, Stockton-on-Tees, all of England

[73] Assignee: Davy McKee (London) Limited, London, England

[21] Appl. No.: 501,928

[22] Filed: Jun. 7, 1983

[51] Int. Cl.$^3$ .............................................. C07C 45/50
[52] U.S. Cl. ................................................... 568/454
[58] Field of Search ........................ 568/454, 883, 909

[56] References Cited

U.S. PATENT DOCUMENTS

| | | | |
|---|---|---|---|
| 3,239,569 | 3/1966 | Slaugh et al. | 568/454 |
| 3,527,809 | 9/1970 | Pruett et al. | 568/454 |
| 3,641,076 | 2/1972 | Booth | 568/454 |
| 3,644,446 | 2/1972 | Booth | 568/454 |
| 3,725,483 | 4/1973 | Deffner et al. | 568/454 |
| 3,733,361 | 5/1973 | Deffner et al. | 568/454 |
| 3,859,359 | 1/1975 | Keblys | 568/454 |
| 3,917,661 | 11/1975 | Pruett et al. | 568/454 |
| 3,933,919 | 5/1976 | Wilkinson | 568/454 |
| 3,956,177 | 5/1976 | Zuech | 568/454 |
| 4,101,588 | 7/1978 | Nienberger et al. | 568/454 |
| 4,158,020 | 6/1979 | Stautzenberger | 568/454 |
| 4,195,042 | 3/1980 | Zuech | 568/454 |
| 4,224,255 | 9/1980 | Smith | 568/454 |
| 4,258,215 | 3/1981 | Dawes | 568/454 |
| 4,267,383 | 5/1981 | Booth et al. | 568/454 |
| 4,306,087 | 12/1981 | Matsumoto | 568/454 |

FOREIGN PATENT DOCUMENTS 1338237 11/1973 United Kingdom ................ 568/454

Primary Examiner—Werren B. Lone
Attorney, Agent, or Firm—Bernard, Rothwell and Brown

[57] ABSTRACT

A process for the production of a non-linear aldehyde by hydroformylation of an optionally substituted internal olefin comprises:
 providing a hydroformylation zone containing a charge of a liquid reaction medium having dissolved therein a complex rhodium hydroformylation catalyst comprising rhodium in complex combination with carbon monoxide and with a cyclic phosphite having a bridgehead phosphorus atom linked to three oxygen atoms at least two of which form together with the bridgehead phosphorus atom part of a ring;
 supplying said internal olefin to the hydroformylation zone;
 maintaining temperature and pressure conditions in the hydroformylation zone conducive to hydroformylation of the internal olefin;
 supplying make-up hydrogen and carbon monoxide to the hydroformylation zone; and
 recovering from the liquid hydroformylation medium a hydroformylation product comprising at least one non-linear aldehyde.

14 Claims, No Drawings

HYDROFORMYLATION PROCESS

This invention relates to a hydroformylation process, particularly a process for the hydroformylation of internal olefins to give non-linear aldehydes.

Hydroformylation is a well known reaction in which an olefin (usually a terminal olefin) is reacted under suitable temperature and pressure conditions with hydrogen and carbon monoxide in the presence of a hydroformylation catalyst to give an aldehyde, or a mixture of aldehydes, having one more carbon atom than the starting olefin. Thus ethylene yields propionaldehyde, whilst propylene yield a mixture of n- and iso-butyraldehydes, of which the straight chain n-isomer is usually the more commercially desirable material. In some cases the catalyst can be modified so that the products are not aldehydes but are the corresponding alcohols.

The catalysts first used in this reaction were cobalt-containing catalysts, such as cobalt octacarbonyl. The use of such catalysts necessitates exceptionally high operating pressures, e.g. several hundred bars, in order to maintain the catalysts in their active form. The n-/iso-molar ratio of the aldehyde products is not particularly high, e.g. about 3:1 or 4:1, and product recovery is generally complicated because the cobalt carbonyl catalysts are volatile and chemically unstable in the absence of high hydrogen and carbon monoxide partial pressures.

Modified forms of cobalt carbonyls have also been described in the literature as hydroformylation catalysts. For example, British Patent Specification No. 988,941 proposes the use as hydroformylation catalyst of a cobalt complex containing at least one biphyllic ligand containing trivalent phosphorus, the three valencies of the phosphorus atom being satisfied with any organic group and the organic group optionally satisfying two of the phosphorus valencies to form a heterocyclic compound. Such complexes yield, however, alchols rather than aldehydes as the major hydroformylation product. Moreover, Example II indicates that, when using 2-pentene as olefin, the major product is the normal alcohol n-hexanol, rather than the iso-alcohol, 2-methyl-1-pentanol.

British Patent Specifications Nos. 1,198,815 and 1,198,816 describe the production and use of hydroformylation catalysts in batch reactions of complexes of cobalt carbonyl and various cyclic phosphorus compounds, including 4-hydro-2,6,7-trioxa-1-phosphabicyclo-[2,2,2]-octane and substituted derivatives thereof. Such complexes are ascribed (see page 25, lines 54 to 63 of British Patent Specification No. 1,198,815) the structural formula:

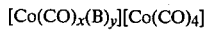

in which B is the cyclic phosphorus compound, x and y are whole numbers from one to 4 and $x+y=5$, and are said to be more thermally stable than cobalt carbonyls. However, their thermal stability is clearly still far from acceptable since it is recommended to employ them, in order to render then even more thermally stable, in admixture with a trialkylamine having a pKa acidity of at least +8 but not greater than '15, e.g. trimethylene, tri-n-butylamine, and the like. Operating temperatures of 93° C. to 246° C. are used, while the pressure can be from 35 to 350 kg/cm² gauge (from about 35.3 to about 355 bar), preferably from 70 to 210 kg/cm² gauge (from about 69.7 to about 207 bar). n-/iso-ratios in the range of from about 4:1 to about 8:1 are said to be obtainable. It is a disadvantage of this process that significant amounts of alcohol rather than aldehyde are produced. Thus in the hydroformylation product, from 5% up to about 25% by weight consists of the alcohol, the balance being the aldehyde (see page 25, lines 97 to 102 of British Patent Specification No. 1,198,815). Moreover the catalyst activity is not very high, contact times of at least 30 minutes being recommended. It is also a feature of the process that polymeric byproducts are formed. This is perhaps a consequence of using aliphatic triamines as additives since these compounds and other basic substances are known to catalyse the self-condensation reactions of aldehydes. Although the process is said to be amenable to hydroformylation of a variety of olefins, including pentene-2, hexene-2, heptene-2 and octene-2, the Examples teach solely the use of terminal olefins, viz propylene and hexene-1.

More recently there have been proposed rhodium complex hydroformylation catalysts for hydroformylation of alpha-olefins, that is to say compounds containing the group $-CH=CH_2$ or $>C=CH_2$. These catalysts generally comprise rhodium in complex combination with carbon monoxide and with a ligand, such as triphenylphosphine and are used in conjunction with excess ligand. Such rhodium complex catalysts are now in use in numerous hydroformylation plants throughout the world and many plants formerly operating with cobalt catalysts have been, or are being, converted for operation with these newer rhodium catalyst. Such catalysts have the advantage not only of lower operating pressures e.g. about 20 kg/cm² absolute (19.6 bar) or less, but also of being capable of yielding high n-/iso-aldehyde product ratios from alpha-olefins; in many cases n-/iso-aldehyde molar ratios of 10:1 and higher can be achieved. Moreover, since the catalyst is non-volatile, product recovery is greatly simplified. A fuller description of the process will be found in the article "Low-pressure OXO process yields a better product mix", Chemical Engineering, Dec. 5, 1977, pages 110 to 115. Also extremely relevant to this process are U.S. Pat. No. 3,527,809 and British Pat. Nos. 1,338,237 and 1,582,010.

The rhodium catalyst adopted in commercial practice comprises rhodium in complex combination with carbon monoxide and with triphenylphosphine. Although the nature of the catalytic species is not entirely clear, it has been postulated to be $HRh(CO)(PPh_3)_3$ (see, for example, page 792 of "Advanced Inorganic Chemistry" (Third Edition) by F. Albert Cotton and Geoffrey Wilkinson, published by Interscience Publishers). The reaction solution contains excess triphenylphosphine and operating temperatures in the range of from about 90° C. to about 120° C. are recommended.

The process of U.S. Pat. No. 3,527,809, which is the process used commercially, is restricted to use of alpha-olefinic compounds such as ethylene, propylene, butene-1, and hexene-1, i.e. compounds with a terminal $-CH=CH_2$ or $>C=CH_2$ group. Although terminal olefins can be successfully hydroformylated in high yield to the corresponding straight chain aldehydes (e.g. propylene can be hydroformylated to n-butaldehyde) using this process, we have found that the use of non-terminal olefins, such as butene-2, with a view to producing the iso-aldehyde (e.g. 2-methylbutyraldehyde from butene-2) is much less successful than with terminal olefins, such as butene-1, because such internal olefins are much less reactive than the corresponding terminal olefins, and higher operating temperatures are hence required in order to achieve acceptable reaction rates and product aldehyde yields. However, the use of higher operating temperatures is accompanied by an increasing tendency for the internal olefin to undergo isomerisation, with a consequent reduction in the yield of the desired iso-aldehyde. Hence, butene-2 tends to undergo isomerisation to butene-1 under the harsher conditions required for hydroformylation of butene-2 so that a proportion of the butene-2 is converted to n-valeraldehyde rather than to the desired iso-butyraldehyde. In addition, the catalyst appears to be less stable at the increased operating temperatures required for adequate reaction rates so that the rate of deactivation of the catalyst becomes undesirably high. For these reasons we consider that rhodium complex catalysts using triphenylphosphine as ligand are not commercially acceptable for hydroformylation of internal olefins.

U.S. Pat. No. 3,527,809 also proposes the use of various other ligands, including phosphites, such as triphenylphosphite, in place of triphenylphosphine. Although the use of triphenylphosphite has the advantage that lower operating temperatures can be used in the hydroformylation of internal olefins, we have found that the catalyst tends to deactivate moderately rapidly, a phenomenon that is accompanied by disappearance of free triphenylphosphite ligand and by an increase in the rate of formation of "heavy" materials (i.e. high boiling byproducts). Further teaching as to the use of phosphites in hydroformylation of terminal olefins will be found in U.S. Pat. Nos. 3,917,661, 3,499,933 and 4,262,142.

There are numerous other references in the literature to the use of phosphite ligands in homogeneous rhodium complex hydroformylation catalysts. Examples include U.S. Pat. Nos. 3,547,964, 3,560,539, 3,641,076, 3,644,446, 3,859,359, 3,907,847, 3,933,919, 3,956,177, 4,096,192, 4,101,588, 4,108,905, 4,135,911, 4,158,020, 4,195,042, 4,224,255 and 4,267,383, as well as British Pat. Nos. 995,459, 1,207,561, 1,228,201, 1,243,189, 1,243,190, 1,263,720, 1,338,225, 1,448,090, 1,455,645, 1,460,870, 1,461,900, 1,462,342, 1,463,947, 1,557,396, and 1,586,805, European Patent Publications Nos. 0003753 and 0028892, and International Patent Publication No. WO 80/00081. Other examples include Japanese Patent Publications Nos. 10765/69 published May 19, 1969 and 40326/73 published Nov. 30, 1973. Although a number of these literature references suggest internal olefins as possible starting materials, none of these references gives any experimental data regarding rhodium catalysed hydroformylation of internal olefins using phosphites as ligands.

Japanese Patent Publication No. 575/66, published Jan. 21, 1966, describes the batch production of 2-methylbutyraldehyde by hydroformylation of butene-2 using rhodium tricarbonyl as catalyst. Pressures of 170 kg/cm$^2$ and higher are used, whilst the temperature is kept below about 80° C.

British Patent Specification No. 2,000,124A describes the production of straight chain aldehydes by catalytic hydroformylation of internal olefins. Example 1 teaches hydroformylation of butene-2 using HRh(CO)(PPh$_3$)$_3$ and Mo(CO)$_6$ as co-catalyst to give an n-/iso-aldehyde molar ratio of 1.6:1, i.e. the major product is n-valeraldehyde. Examples 2 to 10 teach use of HRh(CO)(PPh$_3$)$_2$ and various co-catalysts in hydroformylation of a mixture of 2- and 3-hexenes; the n-/iso-aldehyde ratio is 1.3:1 or greater, i.e. the major product is n-heptaldehyde.

British Patent Specification No. 2,068,377A describes hydroformylation with rhodium catalysts of alpha-olefins and internal olefins using certain fluorinated phosphites as ligand. Examples 4 to 6 and Comparative Example C disclose use of heptene-2 as starting material in batch reactions with production of the iso-aldehyde as the major product. There is, however, no report of continuous operation of the reaction for extended periods.

U.S. Pat. Nos. 4,200,591 and 4,200,592 teach processes for the production of straight chain aldehydes from internal olefins using a rhodium hydroformylation catalyst and a triaryl phosphine or triarylphosphite as ligand in the presence of a co-catalyst of a specified type.

U.S. Pat. No. 4,107,079 describes solid insoluble metallic complexes for use as hydroformylation catalysts which may contain rhodium and a ligand. Amongst ligands suggested are phosphites, including the phosphite of trimethylol propane (column 3 line 61). Example 19 describes hydroformyation of "3-pentene" in a batch reaction with a solid insoluble complex catalyst based upon RhCl(PPh$_3$)$_3$. There is no disclosure of any experimental work with phosphite ligands in the solid hydroformylation catalyst.

Example 2 of British Patent Specification No. 1,325,199 teaches the use, in a batch reaction for the hydroformylation of hexene-1, of the catalyst [RhCl(CO)(tmpP)$_2$] where tmp represents the radical

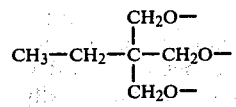

Reaction is effected in the liquid phase using a 50% v/v solution of hexene-1 in benzene. At 100° C. 57 mol% conversion of hexene-1 is said to be achieved in 6 hours under partial pressures of carbon monoxide and hydrogen of 12 atmospheres (about 12 bar) to give a reported yield of aldehydes (based on hexene-1 converted) of 100%, of which 65 mole% is 1-heptanal. According to page 2, lines 55 to 61, catalysts devoid of chlorine are as efficient as those containing it, whilst the process is said to be capable of use with alpha-olefins as well as non-terminal olefins, e.g. butene-2, pentene-2, and hexene-2 (page 2, lines 93 to 101). According to page 5, lines 7 to 12, when using similar catalysts with hexene-2 at 100° C. 35 to 38% of the aldehydes formed is 1-heptanal. Conversions of only 57% in 6 hours are not commercially interesting, nor are terminal aldehydes necessarily the most desirable products obtained by hydroformylating internal olefins.

In all hydroformylation processes there is a possibility of product aldehyde undergoing reduction to the corresponding alcohol. Generally speaking such further reduction is undesirable because not only may this result in a lower yield of the desired aldehyde but also the alcohol can react with the aldehyde product to give high boiling hemi- and di-acetals.

There is accordingly a need to provide a process for the production of iso-aldehydes (and similar non-linear compounds having an aldehyde group attached to a non-terminal carbon atom) by hydroformylation of optionally substituted internal olefins at commercially acceptable rates and with negligible catalyst deactivation under the hydroformylation conditions used, as well as being capable of operation under conditions which do not cause isomerisation of the internal olefin to the corresponding terminal olefin nor significant formation of olefin hydrogenation by-products or aldehyde hydrogenation by-products.

The present invention accordingly seeks to provide a process which is capable of continuous operation for hydroformylation of a wide variety of olefinically unsaturated compounds, containing an internal olefinic bond, at commercially acceptable reaction rates, to give iso-aldehyde type compounds. It further seeks to provide such a process which is characterised by little or negligible catalyst deactivation rates and by low rates of formation of "heavies" (aldehyde condensation by-products). Yet again it seeks to provide a process for rhodium-catalysed hydroformylation of optionally substituted internal olefins which utilises a homogeneous rhodium complex catalyst embodying a phosphorus-containing ligand which is capable of operation for entended periods with little or no degradation of the ligand. The invention also seeks to provide a process in which compounds having internal olefinically unsaturated linkages can be successfully hydroformylated in a homogeneous reaction medium to give the corresponding non linear aldehydes having one more carbon atom than the starting materials, with very limited isomerisation of the starting materials during the course of the reaction to the isomeric compounds with a terminal olefin linkage. It is further sought to provide a hydroformylation process in which the amounts of olefin hydrogenation by-products and of aldehyde hydrogenation by-products are very small.

According to the present invention there is provided a continuous hydroformylation process for the production of a non-linear aldehyde by hydroformylation of an optionally substituted internal olefin which comprises:

providing a hydroformylation zone containing a charge of a liquid reaction medium having dissolved therein a complex rhodium hydroformylation catalyst comprising rhodium in complex combination with carbon monoxide and with a cyclic phosphite ligand having a bridgehead phosphorus atom linked to three oxygen atoms at least two of which form together with the bridgehead phosphorus atom part of a ring;

supplying said internal olefin to the hydroformylation zone;

maintaining temperature and pressure conditions in the hydroformylation zone conducive to hydroformylation of the internal olefin;

supplying make-up hydrogen and carbon monoxide to the hydroformylation zone; and recovering from the liquid hydroformylation medium a hydroformylation product comprising at least one non-linear aldehyde.

The catalyst used in the process of the present invention is a rhodium carbonyl complex comprising rhodium in complex combination with carbon monoxide and with a cyclic organic phosphite ligand having a phosphorus atom in a bridgehead position, which phosphorus atom is linked to three oxygen atoms at least two of which form, together with the phosphorus atom to which they are attached, part of a ring. Preferably this catalyst and the reaction medium are substantially halogen-free. Although the structure of such rhodium carbonyl complexes is not entirely clear, it is postulated that the preferred halogen-free complexes may have the structure:

$RhH_m(CO)_n(L)_p$ in which m is zero, 1 or 2, n and p are each, independently of the other, an integer of from 1 to about 4, and L is a cyclic phosphite ligand as defined above, provided that the sum of m, n and p is from 4 to 6.

The optionally substituted internal olefin contains at least one internal olefinic carbon-carbon double bond (or ethylenic bond) and contains at least 4 carbon atoms. Such compounds have the general formula:

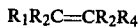

$R_1R_2C=CR_2R_4$ in which $R_1$ and $R_3$ each represent a hydrogen atom or an organic radical or together represent a divalent radical which, together with the indicated carbon atoms, form a non-aromatic carbocyclic or heterocyclic ring, and $R_2$ and $R_4$ each represent an organic radical or together represent a divalent radical which, together with the indicated carbon atoms, for a non-aromatic carbocyclic or heterocyclic ring. (For convenience hereafter the term "internal olefin" is some times used to designate "optionally substituted internal olefin"). Preferably such internal olefins are halogen-free and sulphur-free. Preferably the internal olefin contains from 4 to about 20 carbon atoms. It is especially preferred that the internal olefin shall contain at least one hydrogen atom adjacent to the olefinic double bond, that is to say that the internal olefin is of the formula $R_2C=CHR$ or of the formula $RCH=CHR$, where each R, independently of the others, represents an organic radical.

Illustrative starting olefins include internal olefins, e.g. alkenes, arylalkenes, and cycloalkenes, and substituted internal olefins, e.g. ethers of unsaturated alcohols, and esters of unsaturated alcohols and/or acids.

As examples of internal olefins there may be mentions cis- and trans-butene-2, 2-methylbutene-2, 2,3-dimethylbutene-2, 1,2-diphenylethylene, hexene-2, hexene-3, cis and trans-heptene-2, octene-2, octene-3, octene-4, 3-methylheptene-2, 3-methylheptene-3, 3-methylheptene-5, 3,4-dimethyl-hexene-2, decene-2,tetradecene-2, 4-amyldecene-2, 4-methyltridecene-2, octadecene-2, 6,6-dipropyldecene-3, prop-1-enylbenzene, 3-benzylheptene-3, cyclobutene, cyclopentene, cyclohexene, cycloheptene, cyclooctene, 1-methylcyclohexene, diethyl maleate, diethyl fumarate, crotonaldehyde, crotonaldehyde dimethyl acetal, ethyl cinnamate, cis- and trans-prop-1-enyl t-butyl ether, and the like, as well as a mixture of two or more thereof.

The optionally substituted internal olefin may be supplied to the hydroformylation zone in substantially pure form. Alternatively it may be admixed with one or more alpha-olefins and/or inert materials such as saturated hydrocarbons. In mixtures containing one or more alpha-olefins the internal olefin is the major olefin component.

Besides the internal olefin(s), and possibly also alpha-olefin(s), hydrogen and carbon monoxide, there may be supplied to the hydroformylation one or more inert materials, such as inert gases (e.g. nitrogen, argon, carbon dioxide and gaseous hydrocarbons, such as methane, ethane, and propane). Such inert gases may be present in the internal olefin feedstock or in the synthesis gas. Other insert materials may include hydrogenation byproducts of the hydroformylation reaction, e.g. n-butane where the internal olefin is butene-2.

In many cases the process may be operated so that a part only of the make-up optionally substituted internal olefin, e.g. from about 15% to about 80% or higher, is converted in passage through the hydroformylation zone. Although the process can be operated on a "once through" basis, with unreacted internal olefin being exported beyond battery limits, possibly for other uses, after product recovery, it will usually be desirable to recycle unreacted internal olefin, after product recovery, to the hydroformylation zone. As some isomerisation of internal olefin to the corresponding terminal olefin may occur in passage through the hydroformylation zone (e.g. in the case of butene-2 some isomerisation to butene-1 may occur), the recycle olefin stream may contain a minor amount, typically about 10% or less, of terminal olefin, even though the internal olefin feedstock is substantially free from terminal olefin. In addition it may contain byproduct hydrogenated feedstock. The concentration of internal olefin and of inert materials in the recycle stream or streams can be controlled in the usual way by taking purge streams at appropriate controlled rates.

It is also within the scope of the invention to utilise mixed feedstocks containing both internal and alpha-olefin components. For example, it is possible to use a mixed $C_4$ hydrocarbon feedstock containing, in addition to cis- and trans-butene-2, also butene-1, iso-butylene, n-butene, iso-butane, and minor amounts of $C_{1-5}$ alkanes. In this case the alpha-olefins butene-1 and iso-butylene will be converted to the corresponding aldehydes, i.e. mainly n-valeraldehyde and 3-methylbutyraldehye respectively. In such mixed hydrocarbon feedstocks the major olefin component is the internal olefin, e.g. butene-2.

The organic phosphite ligand is preferably an at least bicyclic compound which contains a phosphorus atom in a bridgehead position linked to three oxygen atoms, each forming part of a cyclic system. Such ligands can be represented by the general formula:

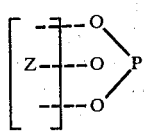
(I)

in which Z represents a trivalent organic group. In formula (I) Z may be acyclic or may comprise a cyclic group; in the former case the ligand of formula (I) is a bicyclic organic phosphite, whilst in the latter case the ligand of formula (I) is a tri- or poly-cyclic organic phosphite. As an example of a ligand of formula (I) in which Z comprises a cyclic group there can be mentioned the compound 2,8,9-trioxa-1-phosphatricyclo-[3.3.1.1$^{3,7}$]-decane of the formula:

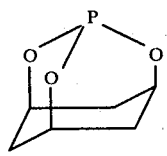
(II)

Other preferred organic bicyclic phosphite ligands are those of the general formula:

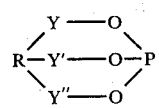
(III)

in which Y, Y' and Y" each, independently of the others, represent a divalent organic radical, and R is a trivalent atom or group. Such compounds can be prepared by the methods described in the literature, for example, by transesterification of an organic phosphite of the general formula:

$(R'O)_3P$ (IV), in which each R' is an optionally substituted alkyl or aryl radical, such as methyl, ethyl, phenyl, benzyl, o-tolyl, naphthyl, hydroxymethyl or hydroxyethyl with a triol or higher polyol of the general formula:

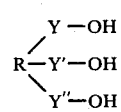
(V)

in which R, Y, Y' and Y" are as defined above. One method of effecting transesterification comprises boiling the phosphite of formula (IV), e.g. triethyl phosphite, under reflux with a triol (or higher polyol) of formula (V), such as trimethylolpropane, optionally in the presence of a transesterification catalyst, e.g. sodium methoxide or triethylamine, and distilling off the alcohol of formula R'OH, e.g. ethanol, as it is formed.

Alternatively the cyclic organic phosphite ligand may be a monocyclic phosphite of the general formula:

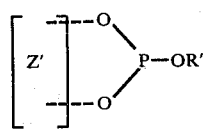
(VI)

in which Z' represents a divalent cyclic or acyclic radical and R' is as defined above. Preferred monocylic ligands are those of the general formula:

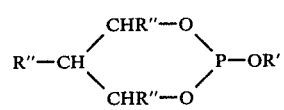
(VII)

in which R" represents a hydrogen atom or one of the meanings of R' (defined above). The compounds of general formula (VI) can be made by methods know in the art for example by transesterification of an organic phosphite of formula (IV) with a diol of formula:

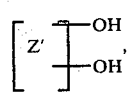
(VI)

in which Z' is as defined above.

In such a transesterification reaction the phosphite of formula (IV), e.g. trimethyl phosphite, triethyl phosphite, or triphenyl phosphite, may be heated under reflux with the diol of formula (VIII), optionally in the presence of a transesterification catalyst. Typical diols of formula (VIII) include 1,3-diols such as propane-1,3-diol and 2,2-dimethylpropane-1,3-diol, and hydrogenation products of alcohols and aldehyde condensation products such as "dimer (V)" of British Patent Specification No. 1,338,237.

As an example of a ligand of formula (VI) there can be mentiond 1-phenoxy-4,4-dimethyl-2,6-dioxa-1-phosphacyclohexane (2,2-dimethyl-propane-1,3-diol phenyl phosphite).

Particularly preferred cyclic phosphite ligands are those in which the bridgehead phosphorus atom forms part of one or more 6-membered rings.

In one preferred mode of operation the cyclic phosphite ligand is introduced as such into the hydroformylation reaction medium. Alternatively the ligand can be formed in situ by charging to the hydroformylation reaction medium a phosphite of a monohydric alcohol or phenol, e.g. trimethyl phosphite, triethyl phosphite, triphenyl phosphite, trinaphthyl phosphite, tri-n-butyl phosphite, tri-n-hexyl phosphite, or the like, and an at least equimolar quantity of an appropriate diol or of a polyol containing three or more hydroxyl groups, such as trimethylol propane or 1,3,5-trihydroxycyclohexane. Transesterification of the phosphite ester with the diol or polyol can be effected by heating the reaction medium, either before or after addition of the rhodium catalyst precursor, and either before or after commencement of hydroformylation.

In formula (III) R may represent, for example

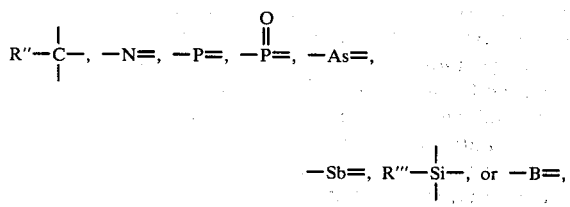

in which R" is as defined above, and R"" is alkyl or alkoxy, e.g. methyl or methoxy. As examples of divalent organic radicals for which Y, Y' and Y" may stand there may be mentioned alkylene, oxy-alkylene, alkylene-oxy-alkylene, alkylene-NR""-alkylene, arylene, oxyarylene, alkylene-arylene, arylene-alkylene, alkylene-oxy-arylene, and arylene-oxy-alkylene; in such groups alkylene may be, for example, methylene, ethylene or ethylidene and arylene may be, for example, o-phenylene or m-phenylene, whilst R"" represents an optionally substituted hydrocarbon radical, such as an alkyl radical. Preferably Y, Y' and Y" contain no more than about 20 atoms in the chain.

Particularly preferred ligands are those of formula (III) in which Y, Y' and Y" are methylene groups or substituted methylene groups, such as ethylidene groups. As examples of ligands of formula (III) there can be mentioned:
2,6,7-trioxa-1-phosphabicyclo-[2,2,2]-octane;
4-methyl-2,6,7-trioxa-1-phosphabicyclo-[2,2,2]-octane;
4-ethyl-2,6,7-trioxa-1-phosphabicyclo-[2,2,2]-octane;
4-hydroxymethyl-2,6,7-trioxa-1-phosphabicyclo-[2,2,2]-octane;
4-ethoxymethyl-2,6,7-trioxa-1-phosphabicyclo-[2,2,2]-octane;
4-acetoxymethyl-2,6,7-trioxa-1-phosphabicyclo-[2,2,2]-octane;
2,6,7-trioxa-1,4-diphosphabicyclo-[2,2,2]-octane;
4-iso-propyl-2,6,7-trioxa-1-phosphabicyclo-[2,2,2]-octane;
4-iso-propyl-3-methyl-2,6,7-trioxa-1-phosphabicyclo-[2,2,2]-octane;
4-n-butyl-2,6,7-trioxa-1-phosphabicyclo-[2,2,2]-octane;
4-n-hexyl-2,6,7-trioxa-1-phosphabicyclo-[2,2,2]-octane;
4-(2-ethylhexyl)-2,6,7-trioxa-1-phosphabicyclo-[2,2,2]-octane;
4-n-decyl-2,6,7-trioxa-1-phosphabicyclo-[2,2,2]-octane;
4-n-undecyl-2,6,7-trioxa-1-phosphabicyclo-[2,2,2]-octane;
3,5,8-trimethyl-2,6,7-trioxa-1-phosphabicyclo-[2,2,2]-octane;
3,4,5,8-tetramethyl-2,6,7-trioxa-1-phosphabicyclo-[2,2,2]-octane;
4-phenyl-2,6,7-trioxa-1-phosphabicyclo-[2,2,2]-octane;
4-cyclohexyl-2,6,7-trioxa-1-phosphabicyclo-[2,2,2]-octane;
4-capryloyloxymethyl-2,6,7-trioxa-1-phosphabicyclo-[2,2,2]-octane;
4-stearoyloxymethyl-2,6,7-trioxa-1-phosphabicyclo-[2,2,2]-octane;
3,5,8-trimethyl-4-phenyl-2,6,7-trioxa-1-phosphabicyclo-[2,2,2]-octane;
4-benzyl-2,6,7-trioxa-1-phosphabicyclo-[2,2,2]-octane;
3,4-dimethyl-2,6,7-trioxa-1-phosphabicyclo-[2,2,2]-octane; and the like.

The rhodium complex catalyst is dissolved in a liquid reaction medium in the process of the invention. This reaction medium comprises, in addition to the catalytic species, product aldehyde(s), aldehyde condensation products, internal olefin, hydrogenation product(s) derived from the internal olefin, and preferably also excess cyclic phosphite ligand. The nature of the aldehyde condensation products, and possible mechanisms for their formation during the course of the hydroformylation reaction, is explained in more detail in British Patent Specification No. 1,338,237, to which reference should be made for further information. Additionally the reaction medium may comprise an added inert solvent, such as benzene, toluene, acetone, methyl isobutyl ketone, t-butanol, n-butanol, tetralin, decalin, ethyl benzoate and the like. Usually, however, it will be preferred to operate in a "natural process solvent", i.e. a mixture of olefinically unsaturated compound, hydrogenation product(s) thereof, aldehyde product(s) and aldehyde condensation products. However, when operating continuously, it may be preferred to use at start up an insert solvent, such as acetone, benzene, toluene, or the like, and then gradually to allow this to be displaced by "natural process solvent" by differential evaporation as the reaction progresses.

The rhodium concentration in the liquid reaction medium may vary from about 10 ppm or less up to about 1000 ppm or more, calculated in each case as rhodium metal and on a weight/volume basis. Typically the rhodium concentration in the liquid reaction medium lies in the range of from about 40 ppm up to about 200 ppm, calculated as rhodium metal. For economic reasons it will not usually be desirable to exceed about 500 ppm rhodium, calculated as metal, in the liquid reaction medium.

In the liquid reaction medium the cyclic phosphite ligand:Rh molar ratio is desirably at least about 1:1. Preferably the ligand:Rh molar ratio is from about 3:1 or 4:1 up to about 20:1 or more. The upper limit of concentration of cyclic phosphite ligand in the reaction medium will usually be about 10% w/v or the solubility limit of the cyclic phosphite ligand therein, whichever is the lower figure. Usually, however, it will be preferred to operate at cyclic phosphite ligand concentrations of less than about 1% w/v and phosphite ligand:Rh molar ratios of from about 5:1 up to about 16:1, e.g. about 8:1. Good results can often be obtained at concentrations of 0.5% w/v or less, e.g. 0.25% w/v or less, of cyclic phosphite ligand.

At least some of the cyclic phosphite ligands used in the process of the invention are highly toxic; extreme care should therefore be taken in handling the phosphite ligands and reaction media containing them.

The hydroformylation conditions utilised in the process of the present invention involve use of elevated temperatures e.g. in the range of from about 40° C. up to about 160° C. or more. Usually, however, it will be preferred to operate at as low a temperature as is possible, consistent with achieving a satisfactory reaction rate, so as to minimise the risk of isomerisation of the internal olefin to a corresponding terminal olefin. Hence preferred operating temperature usually range from about 70° C. up to about 130° C.; such temperatures are usually adequate for internal olefins containing the group —CH=CH—. The reaction rate depends inter alia on the ligand:Rh molar ratio. Hence it will usually be necessary to increase the operating temperature, if the ligand:Rh molar ratio is increased beyond about 8:1, in order to maintain a substantially constant aldehyde productivity. When using ligand:Rh ratios of from about 3:1 to about 8:1, temperatures of about 70° C. to about 100° C. are usually suitable for internal olefins containing the group —CH=CH—; higher temperatures, e.g. up to about 130° C., may be desirable if higher ligand:Rh molar ratios, e.g. about 12:1 or more, are used. Higher temperatures may, however, be necessary where the olefinic carbon-carbon bond is more hindered, as for example when the olefin contains the group —CH=CR— or —CR=CR—, where R is an organic radical (the free valencies indicated in the formulae for these radicals are in each case attached to an organic radical); for example, temperatures up to about 150° C. or higher may be necessary in this case in order to achieve satisfactory reaction rates. Use of such higher operating temperature will usually be accompanied by use of higher ligand:Rh molar ratios, e.g. about 8:1 or higher.

Elevated pressures are also typically used in the hydroformylation zone. Typically the hydroformylation reaction is conducted at a total pressure of from about 4 bar upwards up to about 75 bar or more. Usually it will be preferred to operate at a total pressure of not more than about 35 bar.

In the hydroformylation reaction 1 mole of carbon monoxide and 1 mole of hydrogen react with each internal olefinic bond. Thus, for example, in the case of butene-2, the principal product is 2-methylbutyraldehyde; which is formed by the reaction:

CH$_3$.CH:CH.CH$_3$+H$_2$+CO=CH$_3$.CH(-CHO).CH$_2$.CH$_3$.

A small amount of the isomeric aldehyde, n-valeraldehyde, typically less than 5% of the total aldehydes formed, may also be formed as follows:

CH$_3$.CH:CH.CH$_3$+H$_2$+CO=CH$_3$.CH$_2$.CH$_2$.CH$_2$.CHO.

In addition some of the internal olefins may undergo hydrogenation; hence n-butane may be a byproduct when butene-2 is hydroformylated. Typically less than 5% of the internal olefin undergoes hydrogenation.

In operating the process of the invention in a continuous manner it is desirable to supply make up amounts of hydrogen and carbon monoxide in an approximately 1:1 molar ratio, e.g. about a 1.05:1 molar ratio. The formation of such mixtures of hydrogen and carbon monoxide can be effected by any of the methods known in the art for producing synthesis gas for hydroformylation, e.g. by partial oxidation of a suitable hydrocarbon feedstock such as natural gas, naphtha, fuel oil or coal.

In operating the process of the invention the total pressure of hydrogen and carbon monoxide in the hydroformylation zone can range from about 1.5 bar or less up to about 75 bar or more. The partial pressure of hydrogen may exceed that of carbon monoxide, or vice versa. For example the ratio of the partial pressures of hydrogen and of carbon monoxide may range from about 10:1 to about 1:10. At all events it will usually be desirable to operate at a partial pressure of hydrogen of at least about 0.05 bar up to about 30 bar and at a partial pressure of carbon monoxide of at least about 0.05 bar up to about 30 bar.

Product recovery can be effected in any convenient manner. In some instances, for example when using butene-2 as the olefinically unsaturated compound, it is possible to utilise a gas recycle process similar to that described in British Patent Specification No. 1582010. More usually, however, it will be more convenient to withdraw a portion of the liquid reaction medium from the hydroformylation zone either continuously or intermittently and to distil this in one or more stages under normal, reduced or elevated pressure, as appropriate, in a separate distillation zone in order to recover the aldehyde product(s) and other volatile materials in vaporous form, the rhodium-containing liquid residue being recycled to the hydroformylation zone. Condensation of the volatile materials and separation thereof, e.g. by distillation, can be carried out in conventional manner. Aldehyde product(s) can be passed on for further purification, whilst a stream containing unreacted internal olefin can be recycled to the hydroformylation zone together with any hydrogen and carbon monoxide that was dissolved in the reaction medium. A bleed stream can be taken from the recycle stream or streams in order to control build up of inerts (e.g. N$_2$) and of hydrogenation product(s) in the recycle streams.

The rhodium may be introduced into the reaction zone in any convenient manner. For example, the rhodium salt of an organic acid, such as rhodium acetate, i.e. [Rh(OCOCH$_3$)$_2$.H$_2$O]$_2$, can be combined with the ligand in the liquid phase and then treated with a mixture of carbon monoxide and hydrogen, prior to introduction of the internal olefin. Alternatively the catalyst can be prepared from a carbon monoxide complex of rhodium, such as dirhodium octacarbonyl, by heating with the cyclic phosphite ligand which thereby replaces one or more of the carbon monoxide molecules. It is also possible to start with the ligand of choice and finely divided rhodium metal, or with an oxide of rhodium (e.g. Rh$_2$O$_3$ or Rh$_2$O$_3$.H$_2$O) and the ligand, or with a rhodium salt of an inorganic acid, such as rhodium nitrate (i.e. Rh(NO$_3$)$_3$.2H$_2$O) and the ligand, and to prepare the active species in situ during the course of the hydroformylation reaction. Yet again it is possible to introduce into the reaction zone, as a catalyst precursor, a rhodium complex such as (pentane-2,4-dionato) dicarbonyl rhodium (I) which is then converted, under the hydroformylation conditions and in the presence of excess ligand, to the operative species. Other suitable catalyst precursors include $Rh_4(CO)_{12}$ and $Rh_6(CO)_{16}$.

When using polymeric aldehyde condensation products as solvent, the ratio of aldehyde to such products in the liquid reaction mixture in the hydroformylation zone may vary within wide limits. Typically this ratio lies in the range of from about 1:5 to about 5:1 by weight.

Under appropriate conditions aldehyde productivities in excess of about 0.5 g. moles/liter/hr can be achieved in the process of the invention. Hence it is usually preferred to supply make up internal olefin to the hydroformylation zone at a rate which corresponds to the aldehyde productivity of the system under the hydroformylation conditions selected. As the conversion per pass will usually be less than 100%, typically about 15% to about 80% or higher, it will be necessary to increase correspondingly the feed rate of the make up olefin if the process is to operate on a "once through" basis or to recycle unreacted olefin at an appropriate rate if the process operates with olefin recycle. Often the aldehyde productivity rate exceeds about 1.0 g. mole/liter/hr, e.g. up to at least about 1.5 g. moles/liter/hr and the rate of supply of make up internal olefin must then equal or exceed this value.

In the course of our experiments we have found that, when hydroformylating butene-2 using triphenylphosphine as ligand in a rhodium-catalysed hydroformylation system, it is necessary to raise the reaction temperature to about 120° C. in order to get commercially acceptable rates of hydroformylation. At this temperature, however, significant amounts of butene-2 are isomerised to butene-1, with the result that significant amounts of n-valeraldehyde are produced instead of the desired 2-methylbutyraldehyde. In addition the catalyst loses its activity over a period of time and the reaction solution changes colour from a clear yellow to a muddy brown solution which has little or no catalytic activity. Although the mechanism of deactivation is not entirely clear it is believed that rhodium clusters having phosphido bridges of the type:

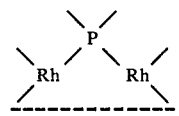

may be formed, this occurring by way of loss of one or more phenyl groups from the triphenylphosphine molecule. (In this formula the free valencies on the rhodium atoms may be attached to at least one other rhodium atom, whilst each of the free valencies on the phosphorus atom is attached either to an organic group, such as phenyl, or to a further rhodium (atom). When triphenylphosphine is replaced by triphenylphosphite reaction commences at lower temperatures, e.g. about 70° C., even with butene-2, but catalytic activity also declines fairly rapidly. Analysis of the reaction medium shows that triphenylphosphite is disappearing from the medium as the reaction proceeds. The at least bicyclic phosphite ligands that are preferably used in the process of the invention, on the other hand, although sharing with triphenylphosphite the great advantage of enabling lower reaction temperatures, of the order of 70° C., to be used even with butene-2, have the additional surprising advantage that they appear to be stable in the reaction medium, even at elevated temperatures, such as about 120° C. or higher. Moreover the rate of formation of aldehyde condensation products and possibly also other "heavies", appears to be lower, when using the cyclic phosphite ligands of the invention, than when using a conventional phosphite ligand, e.g. triphenylphosphite. It was also observed that, when using an at least bicyclic phosphite ligand in the process of the invention, triphenylphosphine appeared to act under certain conditions as a catalyst deactivator.

The invention is illustrated further in the following Examples.

EXAMPLE 1

The continuous hydroformylation of butene-2 was investigated using a stainless steel reactor of nominal capacity 300 ml which is fitted with a magnetically coupled stirrer and with an internal cooling coil through which air could be blown for temperature control purposes. The reactor was also fitted with a gas inlet tube for admission of a $CO/H_2$ mixture to the gas space and an inlet tube for liquid butene-2, each in the form of a dip tube ending near the bottom of the reactor, as well as with a liquid outlet tube in the form of a dip tube whose open lower end was positioned at a level corresponding to the surface level of a volume of 150 ml of liquid in the reactor. Butene-2 was charged to a feed vessel which was pressurised to 4.5 kg/cm² absolute (446 kPa) with $O_2$-free nitrogen and which was connected to the corresponding inlet tube of the reactor by way of a feed pump and a non-return valve. Carbon monoxide and hydrogen were supplied from individual cylinders thereof through individual pressure controllers and then by way of a two channel mass flow controller through an oxygen guard unit (to ensure that the synthesis gas fed to the reactor was oxygen-free).

Liquid in excess of 150 ml together with unreacted gases exited the reactor through the outlet tube and passed through a cooler to a gas-liquid separator which acted as a knock out pot. The gas from the knock out pot was passed through a letdown valve which let its pressure down to atmospheric pressure and was then supplied to a wet gas meter and vented. The separated reactor solution in the knock out pot was maintained at a specific volume using a level controller which let down excess liquid through a capillary tube to a product evaporator consisting of a Liebig condenser packed with Ballotini glass beads. The majority of the liquid passed through the beads and fell into a receiver which was also fitted with a level controller. When this level controller indicated that the liquid in the receiver exceeded a preselected volume hot oil was pumped through the evaporator. The stripped reactor solution was pumped back from the receiver to the reactor at a constant rate by means of a catalyst recycle pump.

The flashed butene-2 and product passed overhead through a cooler to the product receiver, where the majority of the product was collected. Some of the unreacted butene-2 was dissolved in the product condensate whilst the remainder passed on through a meter.

The reactor was heated by immersion in a thermostatically controlled oil bath, fine temperature control being exerted automatically by blowing air on demand through the internal cooling coil. The level controllers were set so that the total liquid inventory of the catalyst containing solution was 200 ml, i.e. an inventory of 50 ml outside the reactor.

To monitor the course of the reaction the gas flow rates were measured and gas chromatographic analyses were performed by sampling the system as follows:

| Sample stream | Components |
|---|---|
| Inlet synthesis gas | $H_2$, CO |
| Exit gas from knock out pot | $H_2$, CO, aldehydes, butenes, butane |
| Butene off gas | $H_2$, CO, butenes, butane, aldehydes |
| Product | Aldehydes, aldehyde by-products, butenes, butane |
| Reactor solution | Aldehydes, aldehyde by-products, butenes, butane, ligand concentration |

$H_2$ and CO were determined using a 1.85 m × 4.76 mm o.d. stainless steel column packed with molecular sieve (5 Å) at 110° C. Butenes and butane were determined using a 1.85 m × 4.76 mm o.d. stainless steel column packed with Porasil C at 60° C. Aldehydes and aldehyde byproducts were determined using a 1.85 m × 4.76 mm o.d. stainless steel column packed with 10% OV 101 on Chromosorb PAW which was temperature programmed to run at 50° C. for 5 minutes and then to increase in temperature at 10° C./minute to 300° C. Ligand concentration was determined using a phosphorus specific flame photometric detector and a 0.46 m × 4.7 mm o.d. stainless steel column packed with 10% OV 101 on Chromosorb PAW run at 220° C.

At start up the empty reactor was purged with nitrogen and then pressurised to 29.2 kg/cm² absolute (2863 kPa) with the CO/$H_2$ mixture and a flow of the hydrogen/carbon monoxide mixture in excess of the anticipated reaction demand was established through the system using the mass flow controllers. Then acetone was charged to the system via the sample point for the product evaporator bottoms using the catalyst recycle pump. When 100 ml of acetone had been charged the reactor stirrer was switched on and adjusted to run at 1500 r.p.m. Once automatic level control had been achieved addition of acetone was terminated. The feedstock pump was then switched on so as to give a butene-2 feed rate of 60 ml/hr and the system allowed to equilibriate under automatic control.

Next 0.1 g $[Rh(OCOCH_3)_2 \cdot H_2O]_2$ (equivalent to 0.418 millimoles of Rh) and 0.3 g (1.8 millimoles) TMPP, i.e. 4-ethyl-2,6,7-trioxa-1-phosphabicyclo-[2,2,2]-octane, were charged to the system via the evaporator bottoms sample point. This corresponds to a TMPP: Rh molar ratio of 4.3:1. When the system was homogeneous the reactor temperature was raised to 98.5° C. Onset of reaction was detected by a decrease in the effluent synthesis gas from the knock out pot, accompanied by more frequent operation of the oil pump to the product evaporator and by the appearance of liquid in the product receiver. As the reaction proceeded the acetone initially charged to the system was replaced within the system by product aldehydes.

The effluent synthesis gas flow rate from the knock out pot was measured to be 22 liters/hr (measured at atmospheric pressure) and its composition was 24% $H_2$, 76% CO. The catalyst solution recycle rate was 270 ml/hr. Results were obtained as set out in Table I below.

TABLE I

| Time (hours) | Aldehyde productivity (g.mol/l.hr.) | Product distribution (%) | | | Butene-2 conversion (%) | Free TMPP level (% w/v) |
|---|---|---|---|---|---|---|
| | | 2-MBAL | VAL | $C_4^+$ | | |
| 21 | 1.11 | 93.5 | 2.5 | 4.0 | 26.5 | 0.099 |
| 33 | 1.12 | 93.2 | 2.6 | 4.2 | 26.8 | 0.103 |
| 45 | 1.21 | 93.8 | 2.5 | 3.7 | 28.8 | 0.105 |
| 57 | 1.11 | 94.0 | 2.2 | 3.8 | 26.4 | 0.095 |
| 69 | 1.11 | 93.1 | 2.4 | 4.5 | 26.7 | 0.109 |
| 81 | 1.11 | 94.1 | 2.3 | 3.6 | 26.4 | 0.101 |

Notes:
2-MBAL = 2-methylbutyraldehyde
VAL = n-valeraldehyde
$C_4^+$ = n-butane
TMPP = trimethylolpropane phosphite (4-ethyl-2,6,7-trioxa-1-phosphabicyclo-[2,2,2]-octane).

COMPARATIVE EXAMPLE A

Using the same general procedure as used in Example 1, except that in place of the rhodium acetate and TMPP there were used 0.36 g $HRh(CO)(PPh_3)_3$, i.e. 0.392 millimoles Rh, and 0.18 g triphenylphosphine, the following results were obtained. As before the pressure was 29.2 kg/cm² absolute (2863 kPa) but the temperature was 85° C. The effluent synthesis gas flow rate from the knock out pot was 25 liters/hr (measured at atmospheric pressure) and this effluent gas analysed as 26% $H_2$ and 74% CO. Results were obtained as shown in Table II (to which the Notes to Table I also apply).

TABLE II

| Time (hrs) | Aldehyde productivity (g.mol/l.hr.) | Product distribution (%) | | | Butene-2 Conversion (%) |
|---|---|---|---|---|---|
| | | 2-MBAL | VAL | $C_4^+$ | |
| 18 | 0.44 | 88 | 11 | 1 | 10.2 |
| 24 | 0.37 | 87 | 12 | 1 | 8.4 |
| 30 | 0.30 | 86 | 13 | 1 | 6.9 |
| 36 | 0.25 | 85 | 14 | 1 | 5.7 |

It will be seen that aldehyde productivity declined at a significant rate with time; such a decline in activity would not be acceptable in a commercial plant. Moreover in excess of 10% of butene-2 was converted to n-valeraldehyde, rather than to the desired product, 2-methylbutyraldehyde. The degree of conversion to n-valeraldehyde also increased as time passed and catalyst activity declined.

COMPARATIVE EXAMPLE B

The procedure of Example 1 was repeated using 0.1 g $[Rh(OCOCH_3)_2 \cdot H_2O]_2$, i.e. 0.418 millimoles Rh, and 0.6 g triphenylphosphite, i.e. 1.93 millimoles. The reactor temperature was 65° C. and the reactor pressure was 29.2 kg/cm² absolute (2863 kPa). The effluent synthesis gas flow rate from the knock out pot was 30 liters/hr (measured at atmospheric pressure) and this analysed as 24% $H_2$, 76% CO. The results obtained are listed in Table III. In determining the free triphenylphosphite ligand level the temperature of the gas chromatography column was 280° C. The Notes to Table I apply also to Table III.

Temperature: 110° C.
Reactor Pressure: 22.15 kg/cm² absolute (2173.5 kPa)
Effluent synthesis gas rate: 25 l/hr.
Effluent synthesis gas composition: 58% $H_2$ 42% CO
Butene-2 feed rate: 60 ml/hr liquid
Liquid recycle rate: 270 ml/hr.
Catalyst: TMPP-3.08 millimoles, i.e. 0.5 g; Rh-0.388

TABLE III

| Time (hours) | Aldehyde productivity (g.mol/l.hr.) | Product distribution % | | | Butene-2 conversion (%) | Free ligand level (% w/v) |
|---|---|---|---|---|---|---|
| | | 2-MBAL | VAL | $C_4^+$ | | |
| 18 | 0.88 | 96.5 | 2.5 | 1.0 | 20.4 | 0.032 |
| 34 | 0.74 | 95.9 | 3.1 | 1.0 | 17.2 | 0.018 |
| 50 | 0.65 | 95.0 | 4.0 | 1.0 | 15.1 | 0.009 |

It will be seen by comparison of Tables I, II and III that, when using TMPP (4-ethyl-2,6,7-trioxa-1 phosphabicyclo-[2,2,2]-octane), the selectivity to 2-methylbutyraldehyde can be maintained above 93% at butene-2 conversions in excess of 26% for extended periods with no reduction in aldehyde productivity and with essentially no decomposition of the ligand. When using triphenylphosphine, however, the selectivity to 2-methylbutyraldehyde was poorer (i.e. 88% or less) and the butene-2 conversion decreased significantly by 44% from 18 hours to 36 hours into the run. This was accompanied by a 43% reduction in aldehyde productivity over the same period. With triphenylphosphite it was clear that the ligand was being destroyed. Although the selectivity to 2-methyl-butyraldehyde was excellent (better than 95%), the butene-2 conversion rate fell appreciably as the run continued, this being accompanied by a corresponding fall in aldehyde productivity.

EXAMPLE 2

The general procedure of Example 1 was repeated except that there were used 0.1 g $[Rh(OCOCH_3)_2 \cdot H_2O]_2$, i.e. 0.418 millimoles Rh, and 0.5 g TMPP (4-ethyl-2,6,7-trioxa-1-phosphabicyclo-[2,2,2]-octane), i.e. 3.08 millimoles. Hence the TMPP:Rh molar ratio was 7.37:1. The reactor pressure was 29.2 kg/cm² absolute (2863 kPa), the butene-2 feed rate was 60 ml liquid/hr and the catalyst solution recycle rate was 270 ml/hr. The reactor temperature was varied during the course of the run with the results obtained being listed in Table IV. As before, the notes to Table 1 apply also to Table IV.

millimoles (as $Rh(CO)_2(AcAc)$, i.e. 0.1 g.)
(Note: TMPP is trimethylolpropane phosphite or 4-ethyl-2,6,7-trioxa-1-phosphabicyclo-[2,2,2]-octane and AcAc is acetylacetone).

After stable operating conditions had been achieved, the reaction was allowed to proceed for 24 hours. The observed productivity was 2.36 g mol/l/hr aldehyde at 54% conversion of butene-2. The reaction solution was pale yellow. Subsequently 3.08 millimoles of triphenylphosphine were added, whereupon the productivity declined sharply to 1.38 g mole/l/hr, and thereafter continued to decline over a period of 12 hrs to 0.56 g mol/l/hr. During this period the solution turned a very dark brown colour.

EXAMPLE 4

Butene-2 was hydroformylated using the general procedure of Example 1 but under the following conditions:

Reactor pressure: 22.15 kg/cm² absolute (2173.5 kPa)
Effluent synthesis gas rate: 29 l/hr, composition: 54% $H_2$ 46% CO
Butene-2 feed rate: 60 ml/hr liquid
Catalyst: TMPP-3.08 millimoles (0.5 g); Rh-0.388 millimoles (as Rh $(CO)_2$ (AcAc), i.e. 0.1 g)
Recycle rate: 270 ml/hr.

The TMPP:Rh molar ratio was thus 7.94:1. The results are summarised in Table V to which the notes to Tables I to IV equally apply. In Table V "ND" means "not determined", whilst the designation "ND*" indicates that the value was not determined but was assumed to be the same as on the last occasion that a determination

TABLE IV

| Time (hrs) | Temp. (°C.) | ESR (l./hr) | ESC | | AP (g mole/l/hr) | Product distribution (%) | | | $C_4^-$ conversion (%) | Free TMPP (% w/v) |
|---|---|---|---|---|---|---|---|---|---|---|
| | | | $H_2$ | CO | | 2-MBAL | VAL | $C_4^+$ | | |
| 30 | 99 | 25 | 90 | 10 | 1.44 | 92.9 | 2.6 | 4.5 | 34.6 | 0.143 |
| 54 | 112 | 36 | 59 | 41 | 2.18 | 91.4 | 2.6 | 6.0 | 53.2 | 0.146 |
| 70 | 112 | 36 | 78 | 22 | 2.49 | 88.8 | 3.0 | 8.2 | 62.7 | 0.149 |
| 91 | 125 | 34 | 82 | 18 | 2.89 | 77.7 | 7.1 | 15.2 | 78.0 | 0.156 |
| 115 | 99 | 25 | 90 | 10 | 1.40 | 93.0 | 2.7 | 4.3 | 33.6 | 0.156 |

Notes:
ESR = Effluent synthesis gas flow rate (measured at atmospheric pressure)
ESC = Effluent synthesis gas composition
AP = Aldehyde productivity
$C_4^-$ = Butene-2
$C_4^+$ = n-Butane

EXAMPLE 3

Following the general procedure of Example 1 the hydroformylation of butene-2 was studied under the following conditions:

was made. For example, in the analyses at 84, 96, 108, 120, and 132 hours it was assumed that the butane yield was still 1.8%, the figure measured after 72 hours.

Analysis of the experimental results showed that the catalyst activity loss, regressed from 48 hours, was only about 0.22% per day.

TABLE V

| Time (hrs) | AP | Temp. (°C.) | Free TMPP (% w/v) | C$_4^-$ conversion (%) | PRODUCT DISTRIBUTION 2-MBAL | VAL | C$_4^+$ | ALDEHYDE RATIO 2-MBAL/VAL |
|---|---|---|---|---|---|---|---|---|
| 12 | 0.86 | 95.3 | N.D. | 19.7 | ND | ND | ND | ND |
| 24 | 1.14 | 95.6 | N.D. | 26.2 | ND | ND | ND | >100 |
| 36 | 1.31 | 95.7 | 0.17 | 30.1 | ND | ND | ND | >100 |
| 48 | 1.42 | 95.7 | 0.15 | 32.6 | ND | ND | ND | >100 |
| 60 | 1.40 | 95.8 | 0.19 | 32.1 | ND | ND | ND | >100 |
| 72 | 1.41 | 95.9 | 0.19 | 32.4 | 97.2 | 1.0 | 1.8 | 98 |
| 84 | 1.44 | 95.7 | 0.16 | 33.0 | 97.1 | 1.1 | ND* | 90 |
| 96 | 1.39 | 95.7 | 0.14 | 31.9 | 97.0 | 1.2 | ND* | 83 |
| 108 | 1.35 | 95.6 | 0.13 | 31.0 | 96.8 | 1.4 | ND* | 70 |
| 120 | 1.38 | 95.5 | 0.16 | 31.7 | 96.7 | 1.5 | ND* | 65 |
| 132 | 1.35 | 95.3 | 0.16 | 31.0 | 96.5 | 1.7 | ND* | 58 |
| 144 | 1.38 | 95.8 | ND | 31.7 | 96.2 | 1.8 | 2.0 | 53 |
| 156 | 1.35 | 95.5 | 0.13 | 31.0 | 96.1 | 1.9 | ND* | 50 |
| 168 | 1.40 | 95.3 | 0.18 | 32.1 | 96.4 | 1.6 | ND* | 59 |
| 180 | 1.31 | 95.3 | 0.13 | 30.1 | ND | ND | 1.7 | ND |
| 192 | 1.43 | 95.2 | 0.14 | 32.8 | 96.7 | 1.6 | ND* | 61 |
| 204 | 1.38 | 95.3 | 0.11 | 31.7 | ND | ND | ND* | ND |
| 216 | 1.38 | 95.6 | 0.16 | 31.7 | 96.8 | 1.5 | ND* | 63 |
| 228 | 1.42 | 95.4 | 0.18 | 32.6 | 96.7 | 1.6 | ND* | 60 |
| 240 | N.D. | 95.2 | 0.16 | ND | ND | ND | ND* | ND |
| 252 | 1.37 | 95.5 | 0.17 | 31.4 | 96.3 | 1.6 | 2.1 | 62 |
| 264 | 1.37 | 95.6 | 0.14 | 31.4 | 96.4 | 1.5 | ND* | 65 |
| 276 | 1.35 | 95.8 | 0.15 | 31.0 | 96.4 | 1.5 | ND* | 63 |
| 288 | 1.44 | 95.7 | 0.14 | 33.0 | 96.2 | 1.7 | ND* | 56 |
| 300 | 1.32 | 95.8 | 0.18 | 30.3 | 96.2 | 1.7 | ND* | 55 |
| 318 | 1.36 | 95.8 | 0.14 | 31.2 | 96.3 | 1.6 | ND* | 62 |

EXAMPLE 5

Another run was carried out using the general procedure of Example 1 under the following conditions:
Pressure: 22.15 kg/cm$^2$ absolute (2173.5 kPa)
Effluent synthesis gas rate: 31 l/hr, composition: 54% H$_2$ 46% CO
Butene-2 feed rate: 60 ml/hr liquid
Catalyst: TMPP-0.778 millimoles (0.126 g); Rh-0.388 millimoles (as Rh(CO)$_2$ (AcAc), i.e. 0.1 g)
Recycle rate: 270 ml/hr.

The TMPP:Rh molar ratio was 2.00:1. The results are summarised in Table VI, to which the rates to Tables I to V also apply. The rate of catalyst activity loss, regressed from 23.5 hours, was 2.9% per day.

TABLE VI

| TIME (HRS) | AP g mol/l/hr | 2-MBAL/VAL ratio | Temp °C. | C$_4^-$ Conversion |
|---|---|---|---|---|
| 5 | 1.07 | ND | 101.9 | 24.6 |
| 6 | 1.19 | ND | 101.8 | 27.3 |
| 7 | 1.21 | ND | 101.9 | 27.8 |
| 11 | 1.41 | ND | 102.3 | 32.4 |
| 15 | 1.38 | 19.8 | 102.2 | 31.7 |
| 19 | 1.46 | 17.8 | 101.9 | 33.5 |
| 22 | 1.57 | ND | 102.0 | 36.0 |
| 23.5 | 1.54 | ND | 102.2 | 35.3 |
| 24.5 | 1.54 | 15.3 | 102.2 | 35.3 |
| 25.5 | 1.55 | 15.4 | 102.1 | 35.6 |
| 26.75 | 1.58 | 15.3 | 102.1 | 36.3 |
| 28 | 1.54 | 15.0 | 102.2 | 35.3 |
| 29 | 1.54 | 15.2 | 102.2 | 35.3 |
| 30 | 1.54 | ND | 102.1 | 35.3 |
| 31 | 1.54 | ND | 102.1 | 35.3 |
| 36 | 1.46 | 14.7 | 101.9 | 33.5 |
| 41.5 | 1.46 | 15.0 | 102.0 | 33.5 |
| 45.5 | 1.50 | 14.8 | 102.2 | 34.4 |
| 47.5 | 1.50 | ND | 102.2 | 34.4 |
| 48.5 | 1.53 | 15.1 | 102.1 | 35.1 |
| 49.5 | 1.54 | ND | 102.1 | 35.3 |
| 50.75 | 1.49 | ND | 102.1 | 34.2 |
| 51.5 | 1.51 | ND | 102.1 | 34.7 |
| 52.5 | 1.50 | 14.8 | 102.2 | 34.4 |
| 53.5 | 1.48 | 14.9 | 102.1 | 34.0 |
| 54.5 | 1.48 | ND | 101.9 | 34.0 |
| 57.5 | 1.46 | ND | 101.7 | 33.5 |
| 60.5 | 1.48 | 14.7 | 102.0 | 34.0 |
| 63.5 | 1.45 | 14.6 | 101.9 | 33.3 |
| 67 | 1.52 | 15.2 | 102.1 | 34.9 |
| 72 | 1.43 | 14.9 | 102.1 | 32.8 |
| 77.5 | 1.44 | ND | 102.0 | 33.0 |

EXAMPLE 6

Butene-2 was hydroformylated according to the general procedure of Example 1 under the following conditions:
Reactor pressure: 22.15 kg/cm$^2$ absolute (2173.5 kPa)
Reactor temperature: 130° C.
Effluent synthesis gas rate: 30 l/hr; composition: 55% H$_2$ 45% CO
Butene-2 -feed rate: 60 ml/hr liquid
Catalyst: TMPP-9.26 millimoles (1.5 g); Rh-0.388 millimoles (as Rh(CO)$_2$ (AcAc), i.e. 0.1 g)
Recycle rate: 270 ml/hr The TMPP:Rh molar ratio was accordingly 23.86:1. The aldehyde productivity was measured to be 1.76 g. moles/L/hr. The butene-2 conversion rate was 40.4% to a product mixture of 89.8% 2-methyl-butyraldehyde, 6.8% n-valeraldehyde, 3.0% n-butane, and 0.4% butene-1.

EXAMPLE 7

The following experiment was carried out to determine the effect of the TMPP:Rh molar ratio on catalyst activity. The same general procedure as described in Example 1 was adopted. The initial operating conditions were:
Reactor pressure: 22.15 kg/cm$^2$ absolute (2173.5 kPa);
temperature: 99° C.
Effluent synthesis gas rate: 23 l/hr, composition: 55% H$_2$ 45% CO Butene-2 flow rate: 60 ml/hr liquid
Catalyst: TMPP-0.389 millimoles (0.063 g); Rh-0.388 millimoles (as Rh(CO)$_2$(AcAc), i.e. 0.1 g)
Recycle rate: 270 ml/hr After stable operating conditions had been achieved the aldehyde productivity rate was determined. Sequential additions of 0.063 g TMPP were made, the productivity of the catalyst being determined after each addition, with the results summarised in Table VII.

TABLE VII

| TMPP/Rh molar ratio | Aldehyde Productivity (g mol/1/hr) |
| --- | --- |
| 1:1 | 1.33 |
| 2:1 | 1.55 |
| 3:1 | 1.73 |
| 4:1 | 1.82 |
| 5:1 | 1.82 |
| 6:1 | 1.72 |
| 7:1 | 1.64 |
| 8:1 | 1.46 |

EXAMPLE 8

Following the general procedure of Example 1, 2-methylbutene-2 was hydroformylated under the following conditions:

Reactor pressure: 22.15 kg/cm$^2$ absolute (2173.5 kPa)
Reactor temperature: 143° C.
Effluent synthesis gas rate: 32 l/hr; composition: 90% H$_2$ 10% CO
2-methylbutene-2 feed rate: 83 ml/hr liquid
Catalyst: TMPP-3.08 millimoles (0.5 g); Rh-0.388 millimoles (as Rh(CO)$_2$(AcAc), i.e. 0.1 g)
Recycle rate: 270 ml/hr The aldehyde productivity was 1.46 g moles/l/hr. The feedstock conversion was 27.8%. The selectivity to aldehydes was 87.5% and that to hydrogenated feedstock was 12.5%.

Effluent synthesis gas composition: 53% H$_2$ 47% CO
Butene-2 feed rate: 60 ml/hr liquid
Catalyst recycle rate: 270 ml/hr.

The nature of the phosphorus components in solution was monitored using the usual gas chromatographic technique with the results indicated in Table VIII.

TABLE VIII

| Time | Phosphorus distribution (%) | |
| --- | --- | --- |
| (hrs) | TMPP | (PhO)$_3$P |
| 0 | 0 | 100 |
| 2.25 | 46 | 54 |
| 8 | 62 | 38 |
| 12 | 88 | 12 |
| 24 | 98 | 2 |

Analysis showed the solution to contain 3.50 millimoles of TMPP (trimethylol propane phosphite) after 24 hours and thus efficient conversion of triphenyl phosphite to TMPP in the reactor. During this run the aldehyde productivity was measured to be 1.38 g moles/litre/hour, with a product distribution of 94% 2-MBAL (2-methylbutyraldehyde), 3% n-valeraldehyde, and 3% n-butane.

EXAMPLE 10

The results tabulated below in Table IX were obtained using the general technique described in Example 1. Conditions were as follows:

Catalyst: 0.1 g [Rh(OCOCH$_3$)$_2$.H$_2$O]$_2$, i.e. 0.418 millimoles Rh and 0.5 g TMPP corresponding to a TMPP:Rh molar ratio of 7.37:1.
Butene-2-feed rate: 60 ml/hr liquid.

The H$_2$ and CO feed rates were adjusted as necessary in order to give a near constant effluent synthesis gas rate and composition. The initial catalyst solution recycle rate was 270 ml/hr. Following each stepwise reduction in catalyst solution recycle rate the system was allowed to stabilise for a number of hours.

TABLE IX

| Time (hrs) | Temp. (°C.) | ESR (l./hr) | ESC H$_2$ | ESC CO | AP (g mole/l/hr) | Product distribution (%) 2-MBAL | VAL | C$_4^+$ | C$_4^-$ conversion (%) | Catalyst solution recycle rate (ml/hr) |
| --- | --- | --- | --- | --- | --- | --- | --- | --- | --- | --- |
| 32 | 99 | 30 | 90 | 10 | 1.47 | 93.1 | 3.2 | 3.7 | 34.3 | 270 |
| 48 | 98.5 | 29 | 89 | 11 | 2.16 | 93.5 | 3.1 | 3.4 | 50.4 | 100 |
| 70 | 100 | 30.5 | 90 | 10 | 2.60 | 93.0 | 2.9 | 4.1 | 61.3 | 50 |
| 91 | 99.5 | 28 | 88 | 12 | 2.84 | 92.5 | 3.2 | 4.3 | 66.4 | 25 |

Notes:
ESR = Effluent synthesis gas flow rate (measured at atmospheric pressure)
ESC = Effluent synthesis gas composition
AP = Aldehyde productivity
C$_4^-$ = Butene-2
C$_4^+$ = n-Butane

EXAMPLE 9

Using the general procedure of Example 1 butene-2 was hydroformylated using the following catalyst:
Triphenylphosphite-3.79 millimoles (1.175 g)
Trimethylolpropane (2-ethyl-2-hydroxymethyl-1,3-propanediol)-75 millimoles (10.05 g)
Rh-0.388 millimoles (as Rh(CO)$_2$(AcAc), i.e. 0.1 g).

After charging acetone to the system these catalyst components were charged sequentially to the apparatus. The hydroformylation reaction conditions were as follows:
Temperature: 110° C.
Pressure: 22.15 kg/cm$^2$ absolute (2173.5 kPa)
Effluent synthesis gas rate: 28 l/hr

EXAMPLE 11

Using the general technique described in Example 1 the hydroformylation of butene-2 was studied under the following conditions:
Temperature: 100° C.
Rhodium concentration: 200 ppm
Ligand: 4-methyl-2,6,7-trioxa-1-phosphabicyclo[2,2,2]-octane
Ligand concentration: 0.25% w/v
Pressure: 22.15 kg/cm$^2$ absolute (2173.5 kPa)
Catalyst solution recycle rate: 72 ml/hr.
Butene-2 feed rate: 60 ml/hr liquid.

After 12 hours from start up the productivity was observed to be 1.51 g mol/l/hr aldehyde. The following selectivities were noted:
  2.7% to n-butane
  12.5% to n-valeraldehyde
  84.8% to 2-methylbutyraldehyde.

EXAMPLE 12

As before, the experimental procedure was as generally described in Example 1. Operating conditions were as follows:
  Temperature: 92° C.
  Rhodium concentration: 200 ppm
  Ligand: 1-phenoxy-4,4-dimethyl-2,6-dioxa-1-phosphacyclohexane (2,2-dimethylpropane-1,3-diol phenyl phosphite)
  Ligand concentration: 0.15% w/v
  Pressure: 22.15 kg/cm$^2$ absolute (2173.5 kPa)
  Catalyst solution recycle rate: 72 ml/hr
  Butene-2 feed rate: 60 ml/hr liquid.
After 20 hours from start up the productivity was observed to be 1.88 g mol/l/hr. The following selectivities were noted:
  3.5% to n-butane
  8.0% to n-valeraldehyde
  88.5% to 2-methylbutyraldehyde.

EXAMPLE 13

Following the general procedure of Example 1 the hydroformylation of butene-2 was investigated using as ligand 4-ethoxymethyl-2,6,7-trioxa-1-phosphabicyclo-[2,2,2]-octane. The conditions were as follows:
  Temperature: 96° C.
  Rhodium concentration: 200 ppm (charged in the form of 0.1 g acetylacetonatodicarbonyl rhodium (I))
  Ligand concentration: 0.25% w/v
  Pressure: 22.15 kg/cm$^2$ absolute (2173.5 kPa)
  Catalyst solution recycle rate: 60 ml/hr
  Butene-2 feed rate: 68 ml/hr liquid.
After allowing the system to stabilise the reaction rate was measured to be 1.52 g mol/l/hr. The conversion of butene-2 per pass was 30.4%. Analysis of the products indicated selectivites to n-butane of 1%, to n-valeraldehyde of 10.3% and to 2-methylbutyraldehyde of 88.7%.

EXAMPLE 14

The procedure of Example 13 was repeated using 4-acetoxymethyl-2,6,7-trioxa-1-phosphabicyclo-[2,2,2]-octane as ligand. The conditions used were as follows:
  Temperature: 97.4° C.
  Rhodium concentration: 200 ppm
  Ligand concentration: 0.25% w/v
  Pressure: 22.15 kg/cm$^2$ absolute (2173.5 kPa)
  Catalyst solution recycle rate: 60 ml/hr
  Butene-2 feed rate: 68 ml/hr liquid.
After 12 hours the reaction rate was measured to be 1.51 g mol/l/hr. The conversion of butene-2 per pass was 29.6%. The following selectivities were noted:
  2% to n-butane
  9.8% to n-valeraldehyde
  88.2% to 2-methylbutyraldehyde.

EXAMPLE 15

The apparatus of Example 1 was used in a "batch" mode to investigate the hydroformylation of a commercially available mixture of octenes. This contained the following isomers:

| C$_8$ Isomer | Double bond position | Concentration % w/w |
|---|---|---|
| n-octene | 1 | 0.2 |
|  | 2 | 2.8 |
|  | 3 + 4 | 3.0 |
| 3-methylheptene |  | 4.0 |
|  | 2 | 24.3 |
|  | 3 | 22.8 |
|  | 5 | 7.7 |
| 3,4-dimethylhexene | 1 | 1.3 |
|  | 2 | 33.0 |
| Others |  | 0.9. |

The catalyst, 0.1 g acetylacetonatodicarbonyl rhodium (I) and ligand, 0.5 g TMPP, were dissolved in 100 ml methyl iso-butyl ketone and charged to the reactor. Subsequently the reactor was topped up with 100 ml of the "octene" mixture via the olefin feed pump. After purging the system the pressure was raised to 22.15 kg/cm$^2$ absolute (2173.5 kPa) with a 1:1 H$_2$:CO mixture. The temperature was then raised to 150° C. and held at this level for six and a quarter hours whilst circulating reactor solution at a rate of 60 ml/hr around the system and without removing any product overhead. The initial reaction rate was 0.6 mol/l/hr but this rate fell as the experiment proceeded. Analysis of the reactor solution indicated that hydrogenation had proceeded to an extent of about 3% whilst the selectivity to aldehyde was about 97%. The "octene" concentration dropped from an initial value of about 56% to about 20% during the course of the run.

EXAMPLE 16

Following the same general procedure described in Example 15 cyclohexene was hydroformylated under the following reaction conditions:
  Temperature: 108° C.
  Rhodium concentration: 200 ppm
  Ligand concentration: 0.25% w/v
  Pressure: 22.15 kg/cm$^2$ absolute (2173.5 kPa)
  Reactor solution recycle rate: 60 ml/hr
  Initial solvent: Acetone
  Initial cyclohexene concentration: 60% v/v
The following results were obtained:

| Time | 1.5 | 2.5 | 3.5 | 4.5 |
|---|---|---|---|---|
| Temperature (°C.) | 107.5 | 108.2 | 108.0 | 107.9 |
| Cyclohexene Concentration (% v/v) | 42 | 29.9 | 21.9 | 16.3 |
| Reaction Rate (g mol/l/hr) | 0.95 | 0.70 | 0.54 | 0.35 |

About 2% hydrogenation and 98% conversion to aldehyde were observed.

I claim:
1. A continuous process for the production of a non-linear aldehyde by hydroformylation of an internal olefin feedstock selected from the group consisting of internal olefins and substituted internal olefins which comprises:
  providing a hydroformylation zone containing a charge of a liquid reaction medium having dissolved therein a complex rhodium hydroformylation catalyst comprising rhodium in complex combination with carbon monoxide and with a cyclic phosphite having a bridgehead phosphorus atom linked to three oxygen atoms at least two of which form together with the bridgehead phosphorus atom part of a ring;

continuously supplying said internal olefin feedstock to the hydroformylation zone;

maintaining in the hydroformylation zone a temperature in the range of from about 40° C. to about 160° C. and a pressure in the range of from about 4 bar to about 75 bar;

supplying make-up hydrogen and carbon monoxide to the hydroformylation zone; and recovering from the liquid hydroformylation medium a hydroformylation product comprising at least one non-linear aldehyde.

2. A process according to claim 1, in which the cyclic phosphite is an at least bicyclic phosphite of the general formula:

$$\left[ Z - \begin{array}{c} --O \\ --O \\ --O \end{array} \right\rangle P \qquad (I)$$

in which Z represents a trivalent cyclic or acyclic organic group.

3. A process according to claim 2, in which the cyclic phosphite ligand is 2,8,9-trioxa-1-phosphatricyclo-[3.3.1.1$^{3,7}$]-decane.

4. A process according to claim 2, in which the cyclic phosphite ligand is selected from 4-methyl-2,6,7-trioxa-1-phosphabicyclo-[2,2,2]-octane, 4-ethyl-2,6,7-trioxa-1-phosphabicyclo-[2,2,2]-octane, 4-ethoxymethyl-2,6,7-trioxa-1-phosphabicyclo-[2,2,2]-octane, and 4-acetoxymethyl-2,6,7-trioxa-1-phosphabicyclo-[2,2,2]-octane.

5. A process according to claim 1, in which the cyclic phosphite is a monocyclic phosphite of the general formula:

$$\left[ Z' \begin{array}{c} --O \\ --O \end{array} \right\rangle P-OR' \qquad (VI)$$

in which Z' represents a divalent cyclic or acyclic organic radical and R' represents an optionally substituted alkyl or aryl radical.

6. A process according to claim 1, in which the internal olefin feedstock is butene-2 and the hydroformylation product comprises 2-methylbutyraldehyde.

7. A process according to claim 1, in which the internal olefin feedstock is supplied to the hydroformylation zone in admixture with a smaller molar amount of an alpha-olefinic compound.

8. A process according to claim 1, in which the hydroformylation zone is maintained at a temperature of from about 40° C. up to about 160° C., at a total pressure of from about 4 bar up to about 35 bar, at a partial pressure of hydrogen and of carbon monoxide each of at least about 0.05 bar, and at a ratio of partial pressures of hydrogen and of carbon monoxide in the range of from about 10:1 to about 1:10.

9. A process according to claim 1, in which the cyclic phosphite ligand:Rh molar ratio is at least about 3:1.

10. A process according to claim 1, in which recovery of the hydroformylation product includes withdrawal of reaction medium from the hydroformylation zone and distillation thereof in one or more stages under normal, reduced or elevated pressure.

11. A process according to claim 10, in which the distillation step yields also a stream comprising unreacted internal olefin feedstock is recycled to the hydroformylation zone.

12. A process according to claim 1, in which the reaction medium comprises aldehyde product and aldehyde condensation products as solvent.

13. A process according to claim 1, in whcih make-up internal olefin feedstock is continuously supplied to the hydroformylation zone at a rate corresponding to at least about 0.5 gram moles per liter of reaction medium per hour.

14. A process according to claim 1, in which the cyclic phospite is formed in situ by transesterification of an organic phosphite of the general formula:

$$(R'O)_3P \qquad (IV)$$

in which each R' is an optionally substituted alkyl or aryl radical with a triol or higher polyol of the general formula:

$$R \begin{array}{c} Y-OH \\ Y'-OH \\ Y''-OH \end{array} \qquad (V)$$

in which Y, Y' and Y" each, independently of the others, represent a divalent organic radical, and R is a trivalent atom or group, or with a diol of the general formula:

$$\left[ Z' \begin{array}{c} -OH \\ -OH \end{array} \right] \qquad (VI)$$

in which Z' represents a divalent cyclic or acyclic radical.

* * * * *

UNITED STATES PATENT AND TRADEMARK OFFICE
CERTIFICATE OF CORRECTION

PATENT NO. : 4,482,749

DATED : 11/13/84

INVENTOR(S) : Alan James Dennis, George Edwin Harrison and James Peter Wyber

It is certified that error appears in the above-identified patent and that said Letters Patent is hereby corrected as shown below:

On the cover page between lines identified by "[22]" and "[51]" insert

--[30] Foreign Application Priority Data
June 11, 1982 [GB] United Kingdom...8217039--

Signed and Sealed this

Eighth Day of October 1985

[SEAL]

Attest:

DONALD J. QUIGG

Attesting Officer

Commissioner of Patents and
Trademarks—Designate